United States Patent [19]

Levy et al.

[11] Patent Number: 5,674,298

[45] Date of Patent: Oct. 7, 1997

[54] CALCIFICATION-RESISTANT BIOPROSTHETIC TISSUE AND METHODS OF MAKING SAME

[75] Inventors: Robert J. Levy, Ann Arbor, Mich.; Eyal Lerner, Ashdod, Israel

[73] Assignee: The Board of Regents of the University of Michigan, Ann Arbor, Mich.

[21] Appl. No.: 478,287

[22] Filed: Jun. 7, 1995

Related U.S. Application Data

[62] Division of Ser. No. 327,359, Oct. 21, 1994, abandoned.
[51] Int. Cl.$^6$ .................................................... A61F 2/02
[52] U.S. Cl. ...................... 8/94.11; 623/1; 623/2; 623/3; 623/4; 623/7; 623/9; 623/10; 623/11; 623/12; 623/13; 623/14
[58] Field of Search ................... 8/94.11; 623/1, 623/2, 3, 4, 7, 9, 10, 11, 12, 13, 14; 514/21

[56] References Cited

U.S. PATENT DOCUMENTS

| | | | |
|---|---|---|---|
| 4,282,322 | 8/1981 | Kahan et al. | 435/119 |
| 4,283,494 | 8/1981 | Kokusho et al. | 435/198 |
| 4,446,122 | 5/1984 | Chu et al. | 424/1.1 |
| 4,690,973 | 9/1987 | Naishiki et al. | 525/54.1 |
| 4,976,733 | 12/1990 | Giradot | 8/94.11 |
| 5,080,670 | 1/1992 | Imamura et al. | 623/2 |
| 5,296,583 | 3/1994 | Levy | 528/72 |
| 5,314,874 | 5/1994 | Miyata et al. | 514/21 |
| 5,436,291 | 7/1995 | Levy et al. | 524/706 |

FOREIGN PATENT DOCUMENTS

| | | |
|---|---|---|
| WO92/09309 | 6/1992 | WIPO . |
| WO94/01481 | 1/1994 | WIPO . |
| WO94/17841 | 8/1994 | WIPO . |

*Primary Examiner*—Alan D. Diamond
*Attorney, Agent, or Firm*—Rohm & Monsanto

[57] ABSTRACT

Naturally-derived bioprosthetic materials are treated with epoxide crosslinking agents. In some embodiments, the tissue is crosslinked with low molecular weight epoxides in aqueous solutions at high pH levels. In other embodiments, the tissue is crosslinked at physiologic pH levels with epoxide crosslinking agents catalyzed with tertiary or quaternary amines, such as Tris or imidazole. In an advantageous embodiment, bioprosthetic tissue is crosslinked and derivatized with an anticalcification agent, such as a polyphosphonate anticalcification agent, using a polyphosphonate:polyepoxide monoadduct.

8 Claims, 6 Drawing Sheets

CALCIFICATION-RESISTANT BIOPROSTHETIC TISSUE AND METHODS OF MAKING SAME

This application is a division of application Ser. No. 08/327,359 filed on Oct. 21, 1994 now abandoned.

BACKGROUND OF THE INVENTION

This invention relates generally to materials which are resistant to in vivo calcification, and more particularly, to methods of preparing calcification-resistant biomaterials, suitable for implantation in a living being, using epoxide crosslinking agents.

More than 100,000 cardiac valve prostheses are placed in patients each year. Frequently, valve replacement surgery is the only means of treating cardiac valve disease. Currently used replacement valves include mechanical valves which may be composed entirely of a synthetic polymeric material such as polyurethane; bioprosthetic valves derived from bovine pericardium or porcine aortic valves; and aortic homografts.

Use of mechanical valves is frequently complicated by thrombosis and tissue overgrowth leading to valvular failure. Bioprosthetic heart valves have improved thrombogenicity and hemodynamic properties as compared to mechanical valve prostheses. However, calcification is the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regurgitation, necessitates re-implantation. Therefore, the use of bioprosthetic heart valves and homografts has been limited because such tissue is subject to calcification. In fact, pediatric patients have been found to have an accelerated rate of calcification so that the use of bioprosthetic heart valves is contraindicated for this group.

Unfortunately, pathologic calcification also further complicates the use of synthetic vascular grafts and other artificial heart devices, such as ventricular assist systems, because it affects the flexibility of the synthetic polymers used to produce the devices.

The mechanism for pathological calcification of cardiovascular tissue is not fully understood. Generally, the term "pathologic calcification" refers to the undesirable deposition of calcium phosphate mineral salts. Calcification may be due to host factors, implant factors, and extraneous factors, such as mechanical stress. There is some evidence to suggest that deposits of calcium are related to devitalized cells, and in particular, cell membranes, where the calcium pump ($Ca^{+2}$—$Mg^{+2}$-ATPase) responsible for maintaining low intracellular calcium levels is no longer functioning or is malfunctioning. Calcification has been observed to begin with an accumulation of calcium and phosphorous, present as hydroxyapatite, which develops into nodules which can eventually lead to valvular failure.

The preparation of bioprosthetic tissue prior to implantation typically includes treatment to stabilize it against subsequent in vivo enzymatic degradation, typically by crosslinking molecules, particularly collagen, on and in the tissue. Various aldehydes have been used for this purpose, including glyoxal, formaldehyde, and glutaraldehyde. Glutaraldehyde, however, is the agent of choice. In addition to fixing the tissue, glutaraldehyde is a good sterilizing agent and it reduces the antigenicity of the tissue. To date, glutaraldehyde is the only effective crosslinking agent for preparing tissues for implantation that can be used at physiologic pH under aqueous conditions. Unfortunately, glutaraldehyde is now known to promote calcification. There is, thus, a need in the art for a means of crosslinking bioprosthetic tissue without promoting calcification.

Non-aldehyde crosslinking agents have been investigated, such as polyepoxides (e.g., polyglycerol polyglycidyl ethers sold under the trademark Denacol by Nagasi Chemicals, Osaka, Japan), but there have been no conclusive studies demonstrating efficacy of polyepoxide cross-linked tissues in vivo.

Research on the inhibition of calcification of bioprosthetic tissue has primarily focussed on tissue pretreatment with either detergents or diphosphonate anticalcification agents. Detergent pretreatment with noncovalently-linked detergents, such as sodium dodecyl sulfate (SDS), and a covalently bound detergent, such as amino oleic acid, have been demonstrated to be efficacious in materials exposed in circulating blood. However, both detergents and diphosphonates tend to wash out of the implanted bioprosthetic tissue with time due to blood-material interactions. Thus, these treatments merely delay the onset of the inevitable calcification process. Accordingly, there is also a need for a means of providing long-term calcification resistance for bioprosthetic heart valves and other implantable biomaterials or devices which are subject to in vivo pathologic calcification.

In addition, detergents disadvantageously affect the tissue, resulting in a diminution of the collagen denaturation temperature, or shrink temperature ($T_s$), which is an important measure of material strength, durability, and integrity. In some cases, use of detergents results in local toxicity. There is, thus, a need for an effective method of imparting anti-calcification properties to bioprosthetic tissues which is not accompanied by the deleterious effects of detergents.

All of the foregoing techniques still result in some degree of pathologic calcification in vivo as measured by calcium content of explanted specimens. There is, therefore, a need for a treatment that results in a greater level of calcification inhibition.

Systemic use of anticalcification agents, such as diphosphonates, results in significant side effects on bone, and overall, growth. There is, therefore, a need for site specific therapy for prevention of pathologic calcification which would offer low regional drug levels and minimal side effects.

It is, therefore, an object of this invention to provide biomaterials for implantation in a mammal which have increased resistance to in vivo pathologic calcification.

It is another object of this invention to provide biomaterials for implantation in a mammal which have a long,term, or prolonged, resistance to in vivo pathologic calcification.

It is also an object of this invention to provide biomaterials for implantation in a mammal which have localized calcification inhibition and, hence, avoid the toxic side effects associated with systemic administration of anticalcification agents.

It is additionally an object of this invention to provide methods of fabricating and/or treating biomaterials for implantation in a mammal using epoxy crosslinking agents to render the biomaterials resistant to in vivo pathologic calcification.

SUMMARY OF THE INVENTION

The foregoing and other objects are achieved by this invention which provides, in one aspect thereof, a biomaterial suitable for implantation in the interior of the body of a living being which has irreversibly bound thereto an effective mount of an epoxide crosslinking agent to stabilize the tissue and block calcification sites thereby rendering said biomaterial substrate resistant to in vivo pathologic calcification.

In another aspect thereof, a biomaterial is crosslinked and derivatized with a polyphosphonate:polyepoxide monoadduct. As used herein, the term "derivatized" means that an anticalcification agent is covalently attached to the surface of biomaterial tissue.

The term "biomaterial" as used herein refers to collagenous material which may be derived from different animal, typically mammalian, species. The biomaterial is typically suitable for implantation, such as bioprosthetic tissue or the like, but the invention should not be limited thereby. Specific examples include, but are not limited to, heart valves, particularly porcine heart valves; aortic roots; walls, and/or leaflets; bovine pericardium; connective tissue derived materials such as dura mater, homograft tissues, such as aortic homografts and saphenous bypass grafts; tendons, ligaments, skin patches, arteries, veins; and the like. Of course, any other biologically-derived materials which are known, or become known, as being suitable for in-dwelling uses in the body of a living being are within the contemplation of the invention.

Any epoxy compound, which is preferably water-soluble and able to function as a calcium antagonist, is within the contemplation of the invention. Examples of suitable epoxide crosslinking agents, include without limitation, mono- or diepoxides, such as diglycidyl butanediol ester, ethanediol diglycidyl ester, erythritol anhydride (EDE), butanediol diglycidyl ether (GAB), and epichlorhydrin, as well as polyfunctional epoxides, such as the epoxides sold under the trademark Denacol by Nagasi Chemicals, Osaka, Japan. The Denacol epoxides are polyfunctional polyglycerol polyglycidyl ethers. For example, Denacol 512 has 4 epoxies per molecule and Denacol 521 has 5 epoxies per molecule. As used herein, the term "polyepoxide" means reactive polyfunctional epoxides having at least two epoxy moieties per molecule.

As used herein the term "polyphosphonate" includes compounds having at least two phosphonates per molecule. Such polyphosphonates are commercially available or can be synthesized by those of skill in the art. Exemplary polyphosphonates include 3-amino-1-hydroxypropane 1,1-diphosphonic acid (APD) and ethanehydroxydiphosphonate (EHDP). In certain embodiments, other polyphosphonates, such as aminomethyltriphosphonic acid and butylpentaphosphonic acid are preferred. Additional illustrative examples include, without limitation, hexamethylenediaminetetra (methylenephosphonic acid) and diethylenetriaminepenta (methylenephosphonic acid). However, other amino-containing anticalcification agents, such as amino derivatives of phosphocitrate, might be suitable for incorporation into the practice of the invention. Additional illustrative examples include, without limitation, hydroxyl, or sulfhydryl derivatives of anticalcification agents.

In one method aspect of the invention, biomaterials are rendered resistant to in vivo calcification by subjecting the biomaterial substrate to polyepoxide pretreatment at high pH so as to form irreversible covalent bonds between the polyepoxide and the biomaterial substrate, both crosslinking and blocking calcification sites.

In another method aspect of the invention, calcification-resistant bioprosthetic tissue is prepared by crosslinking, or fixing, the tissue with an epoxide crosslinking agent at physiologic pH, 7.0–8.0. A catalytic systems enables polyepoxide cross-linking of bioprosthetic tissue at physiologic pH under aqueous conditions. Aqueous solutions of polyepoxides incorporating tertiary or quaternary amine catalysts, for example, have been found to produce calcification-resistant tissues.

In still a further method embodiment of the invention, a monoadduct of a polyphosphonate anticalcification agent and a polyepoxide is formed under conditions where an excess of polyepoxide remains. The excess epoxy crosslinks the tissue and the reactive epoxy functionality of the monoadduct attaches to amino groups of the tissue proteins so as to permanently bind covalently the phosphonate-containing adduct to the tissue.

BRIEF DESCRIPTION OF THE DRAWING

Comprehension of the invention is facilitated by reading the following detailed description, in conjunction with the annexed drawing, in which.

DETAILED DESCRIPTION

Figure 1:
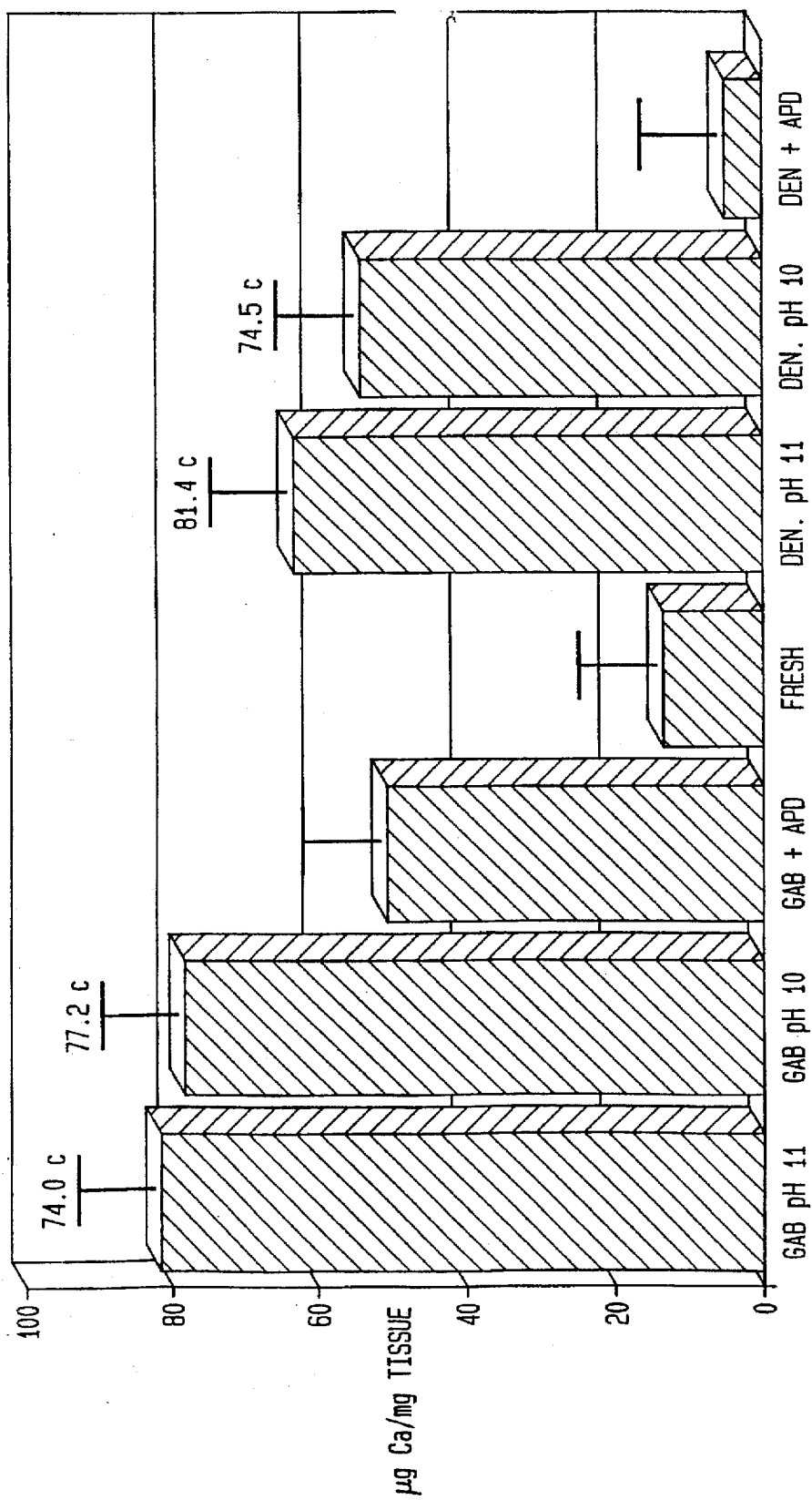
FIG. 1 is a graphical representation of the calcium content (µg/mg) of porcine aortic valve specimens, treated in accordance with methods of the invention, following 21 day subdermal implantation in rats.

Given below are several specific illustrative techniques for producing calcification-resistant bioprosthetic biomaterials in accordance with the principles of the invention. Although the examples given are primarily directed to the preparation of calcification-resistant heart valve components, the techniques described herein are applicable to the creation of any other device, prosthesis or implant comprising biomaterials of the type used for in-dwelling or surgically implanted devices.

I. Crosslinking Bioprosthetic Tissue With Epoxides

A. High pH Processes

In one method embodiment of the invention, fresh bioprosthetic tissue is incubated in an aqueous solution of a water-soluble epoxide crosslinking agent at a pH of 10 or greater for a time sufficient to permit irreversible crosslinking and blocking of calcification sites. The concentration of the epoxide crosslinking agent, which may be a reactive polyfunctional epoxide or diepoxide, preferably ranges from about 0.01M to 1.0M, and more preferably from about 0.05M to 0.5M. The solution is buffered to a pH of greater than 10, and preferably in the range of 10 to 11, in any manner known in the art, illustratively with 0.5M sodium borate.

In preferred embodiments, the incubation time is between about 24 hours and 21 days, typically 7 days. However, the length &time allotted for incubation in the embodiments described hereinabove is illustrative and can be varied by those of skill in the art. It should be noted, however, that no deleterious effects on the bioprosthetic tissue have been observed during the suggested 7 day period. The incubation temperature may range from about 4° C. to 63° C., so that proteins in the tissue will not become denatured. Preferably, the temperature is greater than about 20° C., and most preferably in the range of 25° C. to 37° C.

Bioprostheses such as porcine aortic valve leaflets or bovine pericardium are typically stabilized and preserved in glutaraldehyde following harvesting, illustratively in a 0.2% solution of glutaraldehyde in 0.05 HEPES buffer (N-2-hydroxyethylpiperzine-N'-2-ethanesulfonic acid available from Sigma Chemical Co., St. Louis, Mo.). Glutaraldehyde-preserved bioprostheses can then be stored at 4° C. for prolonged periods of time. In accordance with an advantageous embodiments of the invention, glutaraldehyde-pretreated bioprosthetic tissue which is incubated in aqueous solutions of epoxide crosslinking agents in accordance with the principles of the invention exhibit superior calcification resistance.

In a specific illustrative embodiment, porcine aortic valve leaflets are stabilized and preserved in a high pH (>10, and preferably in the range of 10.5 and 11.5) solution of a low molecular weight epoxide, preferably 4 to 6 carbon atoms in core chain length, such as butanediol diglycidyl ether at 0.1M, at a temperature of 25° C., for 7 days to confer stability and block calcification sites.

B. Physiological pH Processes

In another method embodiment of the invention, bioprosthetic tissue is exposed to an aqueous solution of a water-soluble epoxide crosslinking agent buffered to physiological pH, i.e., a pH in the range of 7.0 to 8.0, preferably 7.4. The crosslinking solution contains a tertiary or quaternary amine which acts as a "catalyst" to enable polyepoxide crosslinking of bioprosthetic tissue at physiologic pH under aqueous conditions. Suitable tertiary or quaternary amines useful in the practice of the invention, include without limitation, Tris(hydroxymethyl)amino methanehydrochloride (Tris), and imidazole. In some embodiments, the catalyst also buffers the solution.

The epoxide crosslinking agent is present in the aqueous solution in a concentration range of 0.005M to 0.5M. The catalyst concentration is typically about 0.01M, but may be varied relative to the concentration of epoxide crosslinking agent. Other reaction conditions, such as time and temperature, are in accordance with the high pH embodiments described hereinabove.

In a specific illustrative embodiment, a polyepoxide, such as Denacol 521 at 0.1M concentration is buffered to pH 7.4 with an 0.01M imidazole or Tris. A bioprosthetic tissue specimen is exposed to the epoxide solution for 7 days at 25° C.

II. Crosslinking and Derivatizing Bioprosthetic Tissue With Polyphosphonate:Polyepoxide Monoadducts In accordance with an advantageous embodiment of the invention, bioprosthetic tissue can be simultaneously crosslinked and derivatized with a polyphosphonate:polyepoxide monoadduct. Polyphosphonate is combined neat with a stock of pure polyepoxide in a molar ratio of at least a 1:2, and preferably 1:10. Under these conditions, a monoadduct of the polyphosphonate:polyepoxide is preferentially formed, leaving excess unreacted polyepoxide. The monoadduct-containing mixture is diluted with water to a concentration in the range of 0.005M to 0.5M, and preferably about 0.1M. In some embodiments, the monoadduct-containing mixture may be buffered to physiologic pH with the catalytic amines, Tris or imidazole, as described above.

Bioprosthetic tissue, either fresh or glutaraldehyde-pretreated, is exposed to the diluted monoadduct-containing mixture for a time sufficient to both crosslink and reactively bind polyphosphonates to the bioprosthetic tissue. More specifically, the monoadduct-containing mixture, which also contains excess unreacted polyepoxide, crosslinks the tissue with the unreacted polyepoxide while the reactive epoxy functionality of the monoadduct attaches to amino groups of the tissue proteins so as to permanently bind covalently the phosphonate-containing adduct to the tissue. The result is permanent calcification resistance.

In an illustrative embodiment of this aspect of the invention, 1M APD is added to 10M of a reactive polyepoxide, such as GAB, and allowed to stand for about 30 minutes to form a monoadduct. The monoadduct solution is diluted with water to 0.1M concentration and buffered to a pH between 7.5 and 10. Fresh bioprosthetic tissue is exposed to the diluted monoadduct solution for a period of 24 hours to 21 days at a temperature of 25° C. to confer crosslinking and derivatization.

It should be noted that the concentration range for the diphosphonate salt (in the pure acid form) is given for purposes of illustration only, and can be varied by those of skill in the art to optimize both binding and cross-linking. Further, the temperature and length of time allotted for incubation in the embodiments described hereinabove is illustrative and can be varied by those of skill in the art.

Moreover, while an aqueous solution is recommended for bioprosthetic tissue inasmuch as organic solvents have deleterious effects on biologically-based tissue, organic solvents are certainly within the contemplation of the invention. Isopropanol and ethanol, for example, have been used safely in connection with bioprosthetic tissues.

Experimental Section

Bioprosthetic Tissue in Rat Subdermal Model

Bioprosthetic tissue samples in the form of bovine parietal pericardium from mature cows were obtained at slaughter and immediately placed in solutions of a low molecular weight epoxide, diglycidylbutanediol ester (GAB), and a high molecular weight epoxide, Denacol 521 (DEN), at pH levels of 10 and 11, for 7 days at 37° C. For comparison, some specimens were also incubated in 0.6% glutaraldehyde, at pH 11, for 7 days at 37° C.

The bovine pericardium samples were implanted in two subcutaneous pouches dissected in the ventral abdominal wall of weanling rats (male, CD, Sprague-Dawley, weighing 50–60 gm). After a period of time (21 days and 60 days), the tissue samples were removed and examined for calcification by measuring the level of $Ca^{+2}$ ions in the tissue. The results are reported below in Table I.

TABLE I

| Epox. | pH | Phos. | Bound Agent at Implant | Implant (days) | $Ca^{2+}$ (µg/mg) |
|---|---|---|---|---|---|
| GAB | 11 | — | — | 21 | 19.0 ± 5.9 |
| GAB | 11 | — | — | 60 | 23.4 ± 10.6 |
| GAB | 10 | — | — | 21 | 61.3 ± 12.4 |
| DEN | 11 | — | — | 60 | 107.8 ± 12.7 |
| GLT | 11 | — | — | 21 | 63.5 ± 7.3 |
| GLT | 11 | — | — | 60 | 109.4 ± 14.6 |

Notes:
GAB = Diglycidylbutanediol ester
DEN = Denacol 521 (polyglycidyl ether-pentaexpoxide)
GLT = Glutaraldehyde Table I shows significant anticalcification inhibition for specimens of bovine pericardium samples treated in low molecular weight epoxides at high pH.

Bioprosthetic tissue samples in the form of porcine aortic valve leaflets were exposed to solutions of GAB and Denacol 521 at pH levels of 10 and 11, for 7 days at 25° C. Other samples were exposed to monoadduct-containing solutions of APD:GAB and APD:Denacol (1M polyphosphonate to 10M polyepoxide) at pH 10 for 7 days at 25° C.

Following exposure to the epoxide crosslinking agents, the leaflet samples were rinsed free of the crosslinking solution and implanted in two subcutaneous pouches dissected in the ventral abdominal wall of weanling rats. After 21 days, the tissue samples were removed and examined for calcification by measuring the level of $Ca^{+2}$ ions in the tissue. The results are shown on FIG. 1 which is a graphic representation of the calcium content, in µg/mg tissue, for each specimen type. Uncross-linked tissue (fresh) is shown for comparative purposes.

Figure 2:
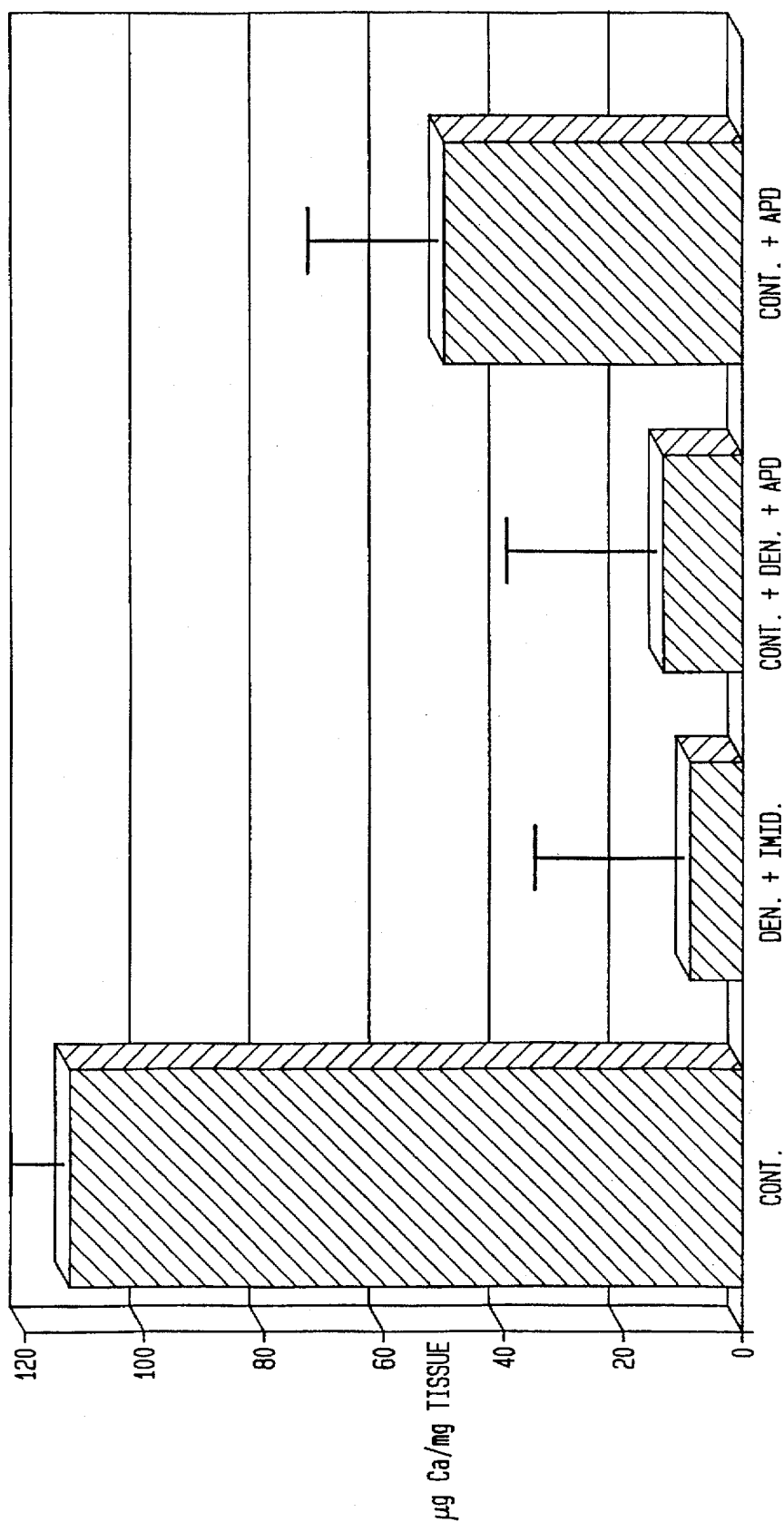
FIG. 2 is a graphical representation of the calcium content (µg/mg) of porcine aortic valve specimens, crosslinked with high molecular weight polyepoxides in accordance with methods of the invention, following 21 day subdermal implantation in rats.

FIG. 2 is a graphical representation of the calcium content (µg/mg) of porcine aortic valve specimens, crosslinked with the high molecular weight polyepoxide, Denacol 521 in accordance with two methods of the invention. In the first method, specimens were exposed to Denacol 521 in an aqueous solution buffered to pH 7.4 with imidazole. In the second method, glutaraldehyde-pretreated specimens were exposed to an aqueous dilution of the monoadduct APD-:Denacol 521 (1:10) buffered to pH 7.4 with imidazole. Control specimens are glutaraldehyde cross-linked in accordance with typical practice in the art. For comparative purposes, glutaraldehyde-pretreated specimens were exposed to the diphosphonate, APD, at pH 7.4. As shown in FIG. 2, following 21 days of implantation in rat subdermal pouches, the specimens treated in accordance with the methods of the present invention contained significantly less calcium than the control.

Figure 3:
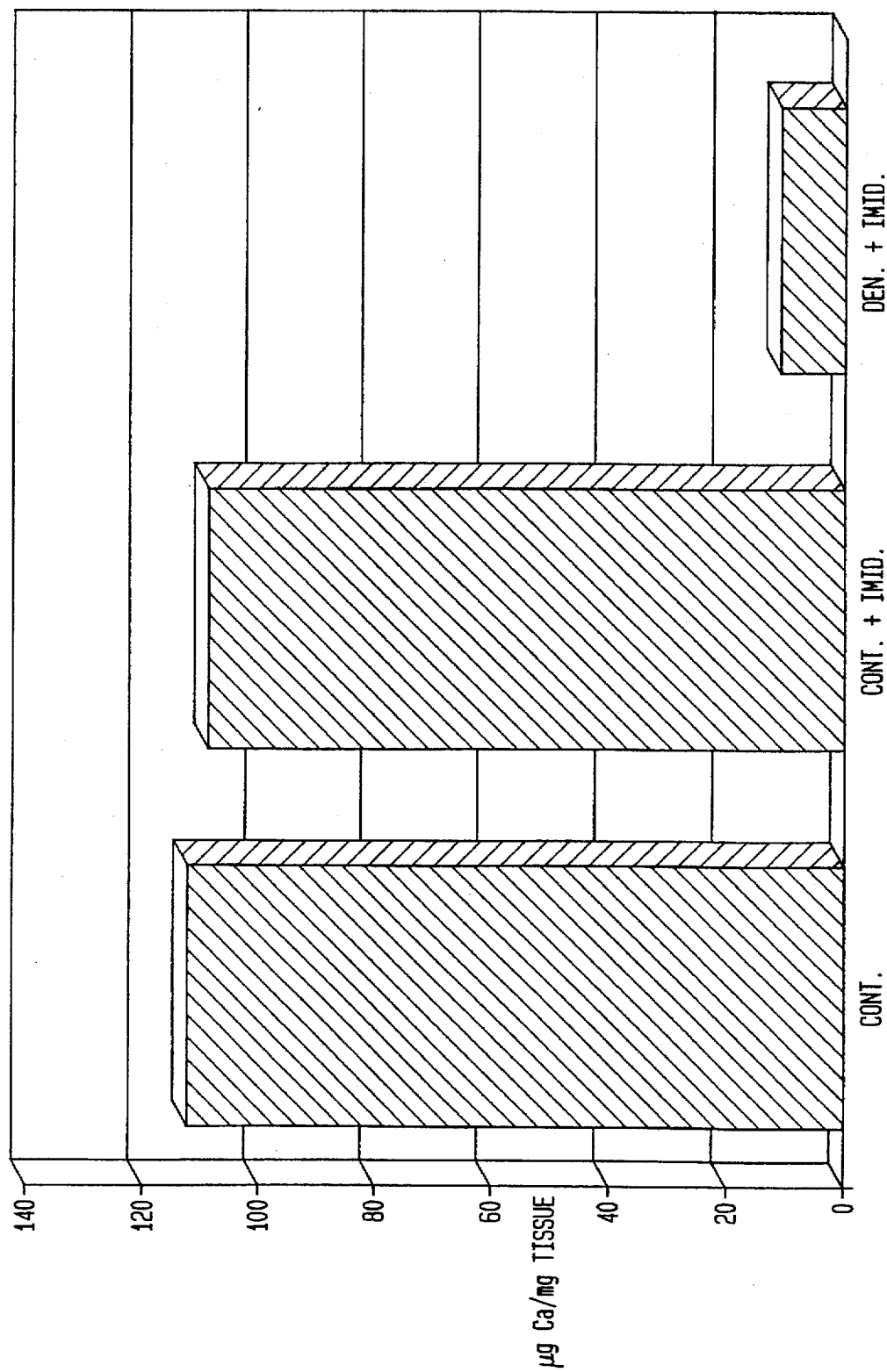
FIG. 3 is a graphical representation of the calcium content (µg/mg) of porcine aortic valve specimens exposed to a catalyst.

In order to demonstrate that the epoxide crosslinking agent is responsible for the calcification resistance, glutaraldehyde-pretreated porcine aortic valve leaflets were placed in aqueous solutions of imidazole at pH 7.4 and Denacol 521 buffered to pH 7.4 with imidazole at 25° C. for 7 days. Glutaraldehyde-pretreated porcine aortic valve tissue comprises the control. FIG. 3 is a graphical representation of the calcium content (µg/mg) of the specimens explanted at 21 days. The imidazole-catalyzed Denacol solution produced significant reductions in calcium content.

Figure 4:
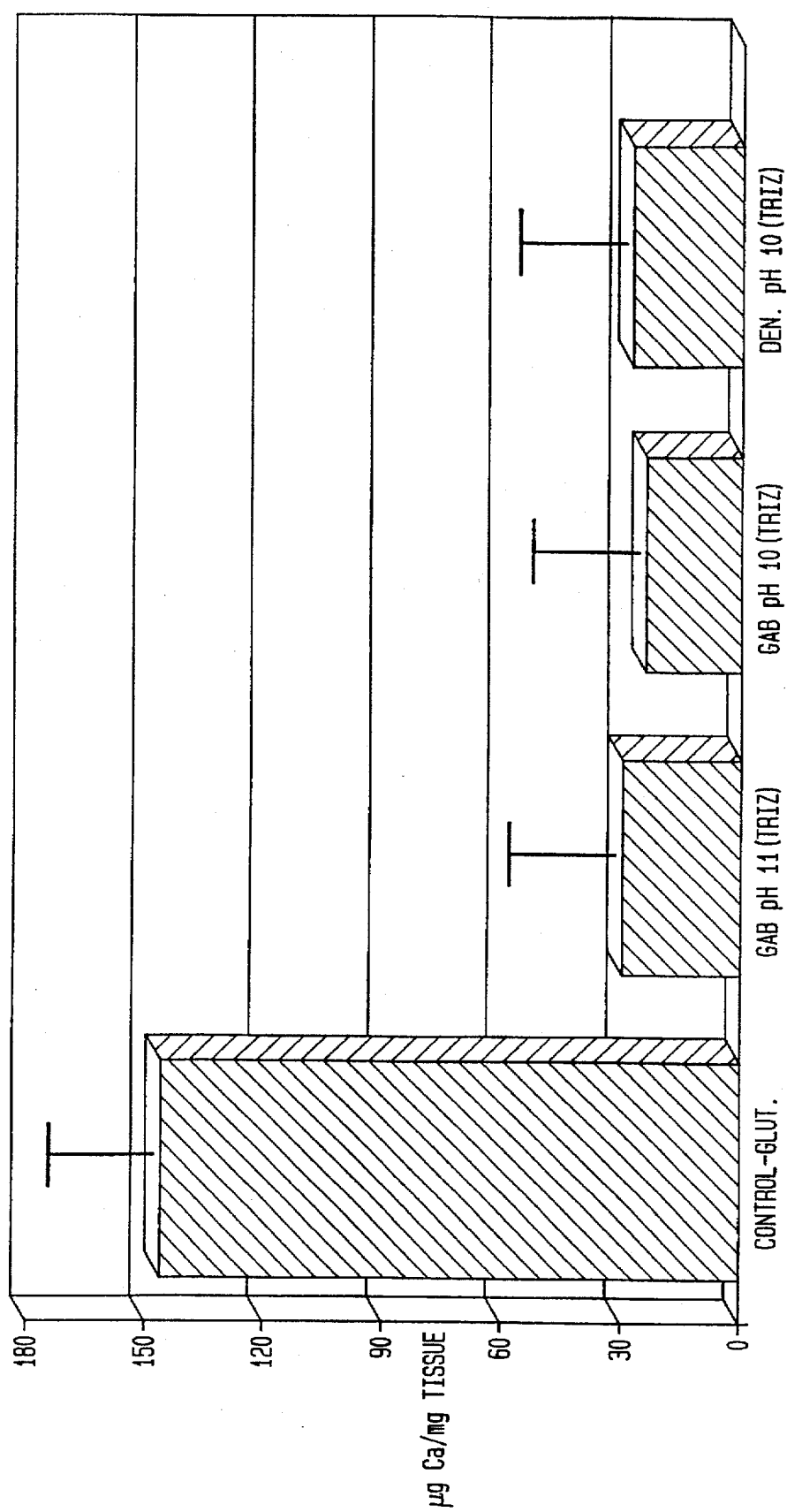
FIG. 4 is a graphical representation of the calcium content (µg/mg) of porcine aortic valve specimens exposed to epoxide crosslinking agents at high pH levels (10–11)in the presence of another catalyst.

FIG. 4 is a graphical representation of the calcium content (µg/mg) of porcine aortic valve specimens exposed to a low molecular weight epoxide (GAB) and a high molecular weight epoxide (Denacol) at high pH levels (10–11, buffered with NaOH) at 25° C. for 7 days in the presence of 0.1M Tris. The inhibitory effect of Tris catalysis is clearly seen when the results of FIG. 4 are compared to FIG. 1 and Table 1.

Figure 5:
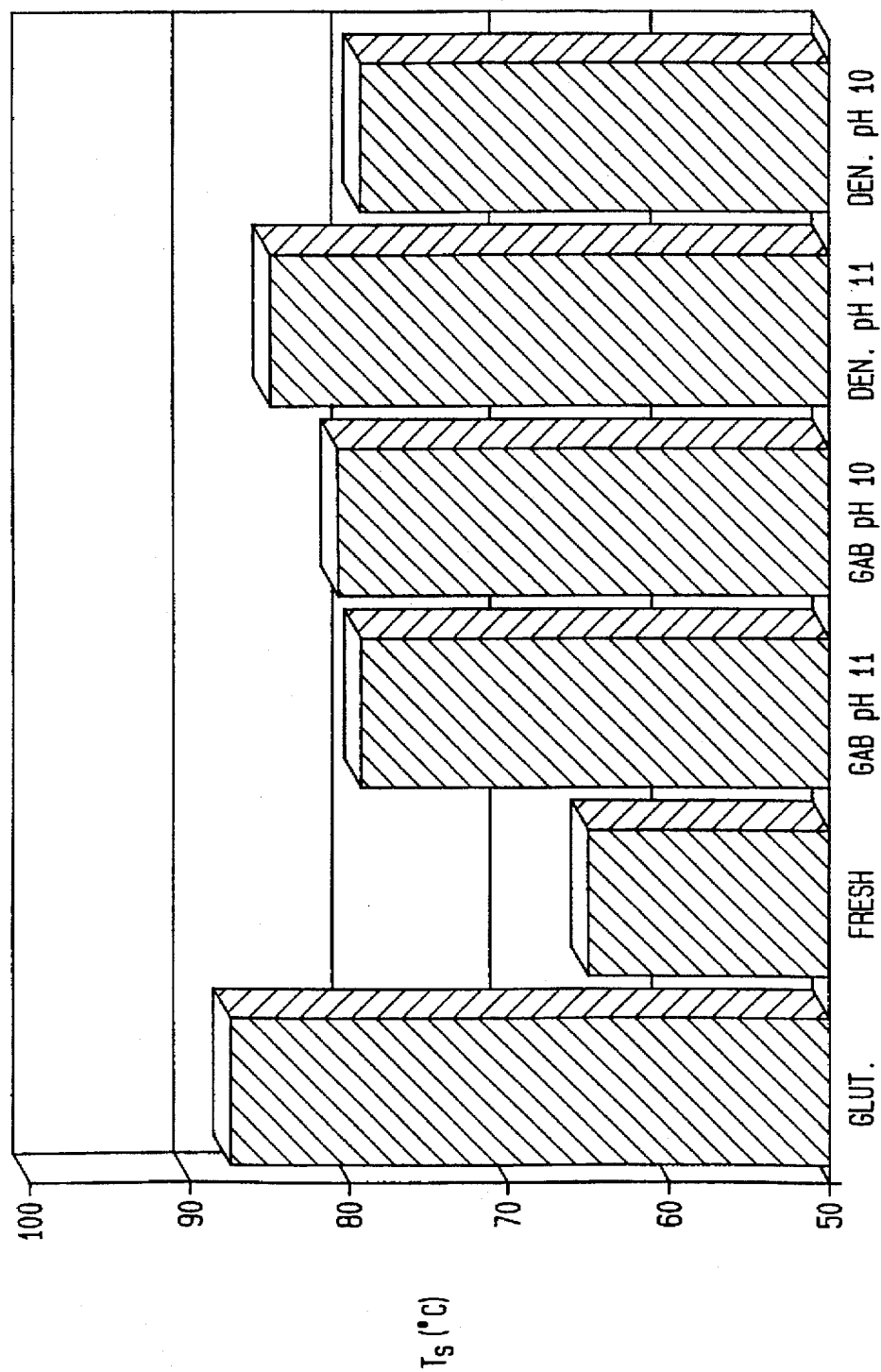
FIG. 5 is a graphical representation of the collagen denaturation temperature (°C.) for specimens of porcine aortic valves leaflets subjected to epoxide crosslinking agents at pH 10 or 11.

FIG. 5 show data demonstrating collagen denaturation temperature or shrink temperature, $T_s$, equivalent to that derived by using glutaraldehyde for porcine aortic valves leaflets subjected to GAB or Denacol at pH 10 or 11 in accordance with the methods of the invention. The collagen denaturation temperature of fresh, untreated leaflets and glutaraldehyde-treated control leaflets are shown for comparison.

Figure 6:
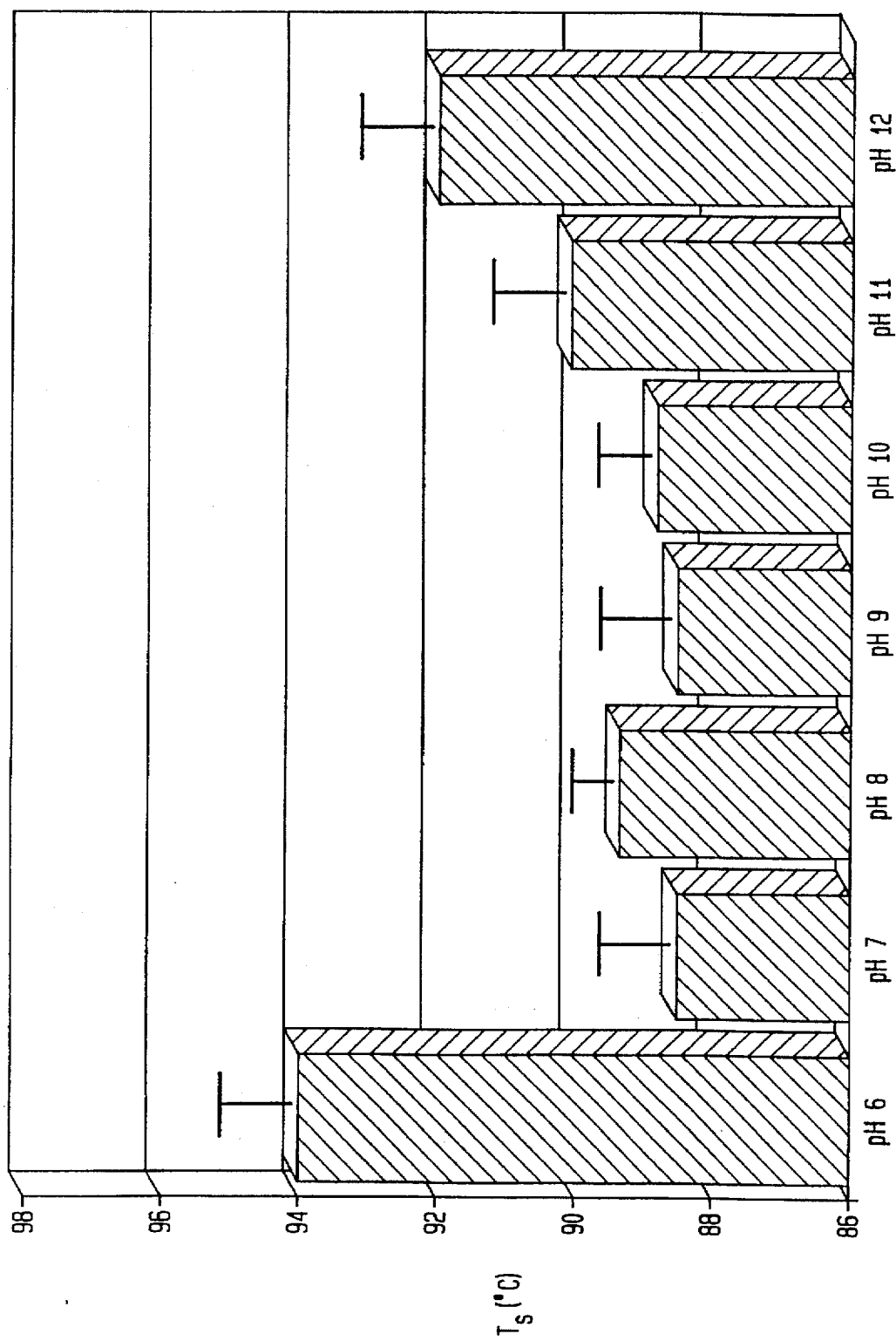
FIG. 6 is a graphical representation of the collagen denaturation temperature (°C.) for specimens of porcine aortic valves leaflets subjected to a polyepoxide crosslinking agent, Denacol, in the presence of a catalyst, at pH levels ranging from 6 to 12.

Furthermore, equally satisfactory shrink temperatures can be attained through using epoxide crosslinking agents at physiologic pH through the use of 0.01M Tris or imidazole. FIG. 6 shows the shrink temperature of porcine aortic valve leaflets exposed for 7 days at 25° C. to an aqueous solution of 0.1M Denacol with 0.01M imidazole, buffered with NaOH to various pHs ranging from 6 to 12. Glutaraldehyde-treated tissue has a shrink temperature at approximately 87° C.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A method of cross-linking bioprosthetic tissue comprising the steps of:
   (a) adding a polyphosphonate anticalcification agent to an excess of a polyepoxide to form a solution of polyphosphonate:polyepoxide monoadduct and excess polyepoxide;
   (b) diluting said solution with water; and
   (c) subjecting bioprosthetic tissue to the diluted solution for a time sufficient to crosslink the bioprosthetic tissue with the excess polyepoxide and to derivatize irreversibly the bioprosthetic tissue with the monoadduct.

2. The method of claim 1 wherein the molar ratio of polyphosphonate to polyepoxide is at least 1:2.

3. The method of claim 2 wherein the molar ratio of polyphosphonate to polyepoxide is 1:10.

4. The method of claim 1 wherein the solution of step (b) is diluted to have a concentration of the monoadduct plus excess polyepoxide ranging from 0.005M to 0.5M.

5. The method of claim 4 wherein the concentration of the monoadduct is 0.1M.

6. The method of claim 7 wherein the diluted solution is buffered with a catalytic amine to a physiologic pH in the range of 7.0 to 8.0.

7. The method of claim 6 wherein the catalytic amine is selected from the group consisting of Tris and imidazole.

8. The method of claim 7 comprising the further step of treating the bioprosthetic tissue with glutaraldehyde prior to said step of subjecting.

* * * * *